United States Patent [19]
Fischer

[11] Patent Number: 4,785,827
[45] Date of Patent: Nov. 22, 1988

[54] SUBCUTANEOUS HOUSING ASSEMBLY

[75] Inventor: David J. Fischer, Arden Hills, Minn.

[73] Assignee: Minnesota Mining and Manufacturing Company, St. Paul, Minn.

[21] Appl. No.: 7,722

[22] Filed: Jan. 28, 1987

[51] Int. Cl.⁴ .............................................. A61N 1/00
[52] U.S. Cl. .................................... 128/783; 128/903; 128/420.6; A61N/1/00
[58] Field of Search ................ 361/331, 380, 395; 174/52 FP; 128/419 P, 642, 631, 673, 748, 120.6, 696, 419 E, 419 G, 783, 784, 789, 903; 604/891.1; 623/10, 11, 24, 25; 340/870.1

[56] References Cited

U.S. PATENT DOCUMENTS

| | | | |
|---|---|---|---|
| 4,237,895 | 12/1980 | Johnson | 128/419 PG |
| 4,301,324 | 11/1981 | Kumar et al. | 174/52 FP |
| 4,314,562 | 7/1982 | Ware | 128/419 P |
| 4,616,655 | 10/1986 | Weinberg et al. | 128/419 P |
| 4,626,960 | 12/1986 | Hamano et al. | 361/395 |

Primary Examiner—Francis Jaworski
Assistant Examiner—George Manuel
Attorney, Agent, or Firm—Donald M. Sell; William L. Huebsch; Stephen W. Bauer

[57] ABSTRACT

A housing assembly for electronic circuitry that can be used subcutaneously. The housing assembly comprises container and base subassemblies each comprising a ceramic portion and a continuous metal sealing flange having a first portion brazed to the ceramic portion around its periphery, and a second portion spaced from the ceramic portion. The ceramic portion of the container subassembly is dish-like to define a cavity, and has a plurality of electric leads brazed to and extending through it. Electronic components are placed in the cavity and attached to the leads, after which the sealing flanges are nested together and welded together along the distal edges of their second portions to close and seal the housing assembly.

11 Claims, 1 Drawing Sheet

SUBCUTANEOUS HOUSING ASSEMBLY

TECHNICAL FIELD

The present invention relates to housings for electronic circuitry adapted to be used subcutaneously.

BACKGROUND ART

Various types of housings have been used for electronics intended to be placed beneath the skin of a person such as the radio frequency receiver included in a cochlear implant of the type described in U.S. Pat. No. 4,352,960 incorporated herein by reference.

One such housing has been of titanium which interferes with transmission of high frequency signals.

Epoxy encapsulant has been used for housing the receiving coil and electronics, but because it does not provide a hermetic seal, eventually body fluids will attack and degrade the electronics.

DISCLOSURE OF INVENTION

The present invention provides a housing assembly for electronics intended to be placed beneath the skin of a person, which housing assembly will appear essentially transparent to radio frequencies, and is essentially immune to attack by body fluids over an extended period of time.

According to the present invention there is provided a housing assembly including container and base subassemblies, each of which subassemblies comprises (1) a ceramic portion having inner and outer surfaces and a periphery at the juncture of the surfaces; and (2) a continuous metal sealing flange having first and second portions, the first portion being bonded or brazed to the ceramic portion along its entire length around the periphery of the ceramic portion and the second portion being spaced from the ceramic portion. The ceramic portion of the container subassembly is dish-like with its inner surface defining a cavity, and has a plurality of electric leads brazed to and extending therethrough between its inner and outer surfaces. The second portions of the sealing flanges are adapted to be positioned closely adjacent with the inner surfaces of the ceramic portions adjacent and to be bonded or welded together (e.g., by laser or electron beam welding) entirely around the sealing flanges.

Preferably the first and second portions of the sealing flanges are disposed generally at a right angle to each other with each of the first portions being disposed in a single plane and projecting toward the center of the subassembly in which it is included and each of the second portions of the sealing flanges being generally cylindrical; and the first and second portions of the sealing flange on the base subassembly are adapted to nest with the first and second portions of the sealing flange on the container subassembly with the second portions projecting along the periphery of the ceramic portion of the base subassembly.

Also, preferably, the sealing flanges are formed from a metal selected from the group consisting of platinum, niobium, titanium and tantalum with niobium being preferred because it has essentially the same coefficient of thermal expansion as the ceramic; the ceramic contains a high percentage of alumina (e.g., 95 to 99 percent); and the sealing flanges are brazed to the ceramic portions using gold with a platinum primer.

The method for forming the novel housing assembly described above comprises the steps of providing the two ceramic portions, one of which is dish-like with its inner surface defining the cavity and has a plurality of through openings extending therethrough between its inner and outer surfaces; and providing the two continuous metal sealing flanges. The first portion of each of the flanges is brazed along its entire length around the periphery of a different one of the ceramic portions with its second portion spaced from the ceramic portion; and wire leads (e.g., of platinum or platinum/iridium) are inserted through the openings in the dish-like ceramic portion and are also brazed to the dish like ceramic portion where they pass through the openings. Such brazing of the sealing flanges and the leads to the ceramic, which requires high temperatures in the range of 1400° to 1600° C., is done prior to placing electronic components in the cavity so that the components will not be damaged by the heat required for such brazing. Subsequently, electronic components (such as radio frequency receiving circuitry including a receiving coil) are positioned in the cavity and connected to the leads; the second portions of the sealing flanges are positioned closely adjacent with the inner surfaces of the ceramic portions adjacent; and the second portions of the sealing flanges are laser or electron beam welded together entirely around the sealing flanges. Such welding can be done without heating the electronic components excessively because of the separation of the second portions of the sealing flanges from the ceramic portions, and that separation also restricts vaporization of the ceramic by the weld beam, which, if it occurred, could cause a flaw in the weld between the sealing flanges.

BRIEF DESCRIPTION OF THE DRAWING

The present invention will be further described with reference to the accompanying drawing wherein like reference numerals refer to like parts in the several views, and wherein.

DETAILED DESCRIPTION

Figure 1:
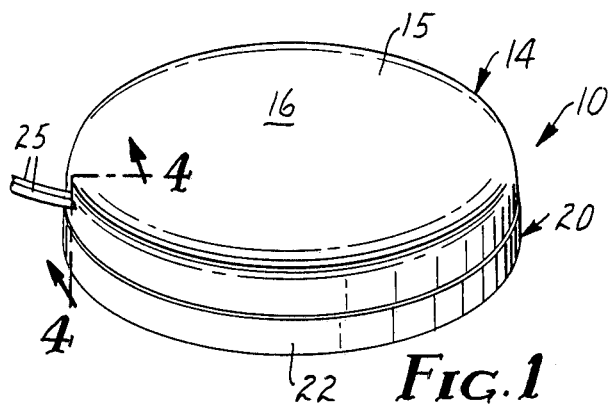
FIG. 1 is a view in perspective of a housing assembly according to the present invention.
Figure 2:
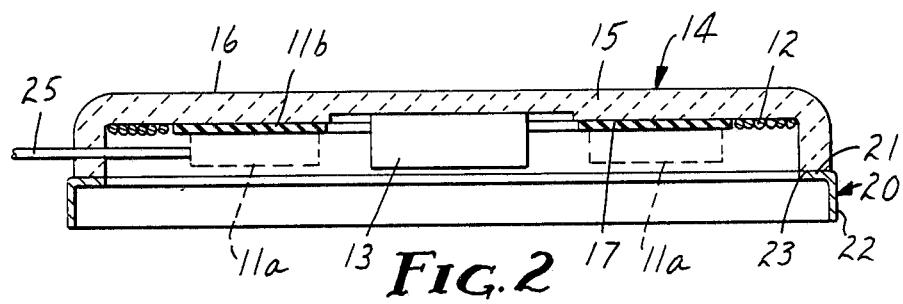
FIG. 2 is an enlarged cross sectional view of a container subassembly included in the housing assembly shown in FIG. 1.
Figure 3:
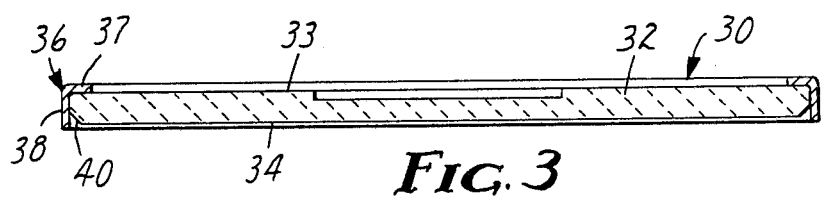
FIG. 3 is an enlarged cross sectional view of a base subassembly included in the housing assembly shown in FIG. 1.

Referring now to the drawing there is shown a housing assembly according to the present invention, generally designated by the reference numeral 10. The housing assembly 10 is adapted for receiving electronic circuitry (such as radio frequency receiving circuitry 11a on a washer-like base 11b and including the receiving coil 12 illustrated in FIGS. 2 and 4) together with a magnet 13 such as is described in U.S. Pat. No. 4,352,960 for holding a sending unit adjacent the housing 10, and can then be welded shut and used subcutaneously.

The housing assembly 10 comprises a container subassembly 14 comprising (1) a dish-like ceramic portion 15 having an outer surface 16, an inner surface defining a cavity 17, and a periphery at the juncture of the surfaces: and (2) a continuous metal sealing flange 20. The metal sealing flange 20 includes first and second portions 21 and 22 disposed at about a right angle to each other. The first portion 21 of the sealing flange 20 is disposed generally in a single plane, projects toward the center of the container subassembly 14, and is brazed along its entire length to a lip 23 around the periphery of the ceramic portion 15. The second portion 22 of the sealing flange 20 is generally cylindrical and projects away from the ceramic portion 15 so that the second portion 22 of the sealing flange 20 is spaced from the ceramic portion 15. A plurality of electric leads 25 (e.g., of platinum or platinum/iridium) are brazed to and extend through the ceramic portion 15 between its inner and outer surfaces.

The housing assembly 10 also comprises a base subassembly 30 comprising (1) a plate-like ceramic portion 32 having generally planar inner and outer surfaces 33 and 34 and a periphery at the juncture of the surfaces 33 and 34; and (2) a continuous metal sealing flange 36. The metal sealing flange 36 includes first and second portions 37 and 38 disposed at about a right angle to each other. The first portion 37 is disposed generally in a single plane, projects toward the center of the base subassembly 30, and is brazed to the ceramic portion 32 along its entire length around the periphery of the ceramic potion 32. The second portion 38 is generally cylindrical and projects along, while being slightly spaced from, the peripheral edge surface of the ceramic portion 32. A peripheral edge 40 of the ceramic portion 32 opposite its inner surface is chamfered so that the distal edge of the second portion 38 is particularly well spaced from the ceramic portion 32.

Figure 4:
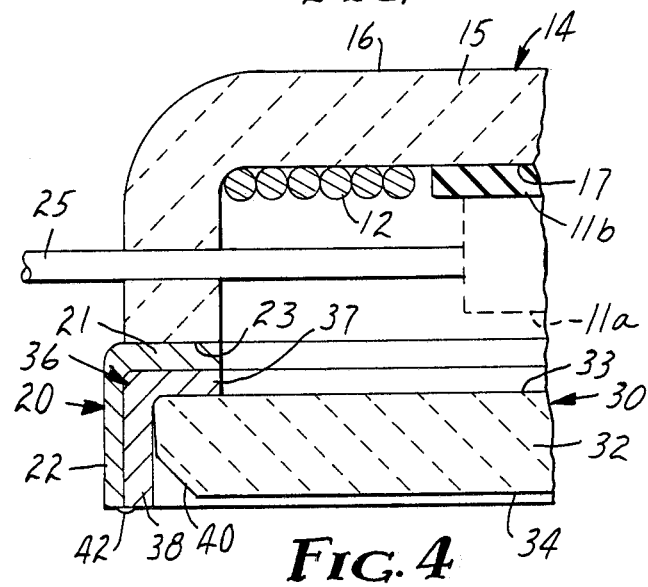
FIG. 4 is an enlarged fragmentary cross sectional view taken approximately along line 4—4 of FIG. 1.

As is best seen in FIG. 4, the first and second portions 37 and 38 of the sealing flange 36 on the base subassembly 30 are adapted to nest with the first and second portions 21 and 22 of the sealing flange 20 on the container subassembly 14 with the inner surfaces of the ceramic portions 15 and 32 adjacent, and the second portions 22 and 38 of the nested sealing flanges 36 and 20 positioned closely adjacent and projecting along the periphery of the ceramic portion 32 of the base subassembly 30 to a position with their distal edges generally aligned and spaced from the ceramic portion 32 where they can be laser or electron beam welded together entirely around the sealing flanges 20 and 36 to form a weld bead 42.

Preferably, the sealing flanges 20 and 36 are formed from a metal selected from the group consisting of platinum, niobium, titanium and tantalum with niobium being preferred because it has a coefficient of thermal expansion essentially equal to that of the ceramic portions 15 and 32; the ceramic portions 15 and 32 contain a high percentage of alumina (i.e., 95 to 99 percent); and the sealing flanges 20 and 36 are brazed to the ceramic portions 15 and 32 using gold with a platinum primer on the ceramic portions 15 and 32.

A preferred method for forming the housing assembly 10 comprises the steps of (1) providing the two ceramic portions 15 and 32 described above with the ceramic portion 15 having a plurality of through openings adapted and positioned to receive the leads 25; and providing the two metal sealing flanges 20 and 36; (2) brazing the first portion 21 or 37 of each of the flanges 20 or 36 along its entire length around the periphery of a different one of the ceramic portions 15 or 32 with its second portion 22 or 38 spaced from the ceramic portion 15 or 32 as described above; (3) inserting the wire leads 25 through the openings in the dish-like ceramic portion 15; (4) brazing the leads 25 to the dish-like ceramic portion 15 where they pass through the openings; (5) positioning electronic components such as the radio frequency receiving circuitry 11a including the coil 12 in the cavity and connecting the electronic components to the leads 25; (6) positioning the second portions 22 and 38 of the sealing flanges 20 and 36 closely adjacent with the inner surfaces of the ceramic portions 15 and 32 adjacent; and (7) welding the second portions 22 and 38 together entirely around the sealing flanges 20 and 36 adjacent the aligned distal edges of the second portions 22 and 38 using laser or electron beam welding. Such brazing of the sealing flanges 20 and 36 and the leads 25 to the ceramic portions 15 and 32, which requires high temperatures in the range of 1400° to 1600° C., is thus done prior to placing electronic components in the cavity 17 so that the components will not be damaged by the heat required for brazing. Such laser or electron beam welding of the sealing flanges 20 and 36 can then be done without heating the electronic components in the cavity 17 excessively because of the separation of the second portions 22 and 38 of the sealing flanges 20 and 36 from the ceramic portions 15 and 32, with that separation also restricting vaporization of the ceramic portions 15 and 32 by the welding beam, which, if it occurred, could cause a flaw in the weld between the sealing flanges 20 and 36.

The present invention has now been described with reference to one embodiment thereof. It will be apparent to those skilled in the art that many changes can be made in the embodiment described without departing from the scope of the present invention. For example, while the embodiment of the housing assembly illustrated is particularly adapted for use with cochlear implants, the housing assembly could be made in other sizes and used in many other places in human or animal bodies to contain many types of electronics. Thus the scope of the present invention should not be limited to the structures described in this application, but only by structures described by the language of the claims and the equivalents of those structures.

I claim:

1. A housing assembly adapted for receiving electronic circuitry, which housing assembly can be sealed shut and used subcutaneously, said housing assembly comprising:

a container sub assembly and a base sub assembly each comprising:

a ceramic portion having a periphery and inner and outer surfaces melting at said periphery and a continuous metal sealing flange having first and second portions, said first portion being bonded to said ceramic portion along its entire length around said periphery and said second portion being spaced from said ceramic portion;

the ceramic portion of said container sub assembly being dish-like with its inner surface defining a cavity, and having a plurality of electric leads brazed to and extending therethrough between said inner and outer surfaces; and said second portions of said sealing flanges being adapted to be positioned closely adjacent with the inner surfaces of said ceramic portions of said sub assemblies facing each other and to be bonded together entirely around said sealing flanges.

2. A housing assembly according to claim 1 wherein the first and second portions of said sealing flanges are disposed generally at a right angle to each other with each of said first portions being disposed in a single plane and projecting toward the center of the subassembly in which it is included, and said first and second portions of the sealing flanges on said base subassembly are adapted to nest with the first and second portions of the sealing flange on said container subassembly with said second portions projecting along the periphery of the ceramic portion of said base subassembly.

3. A housing assembly according to claim 2 wherein said second portions of said sealing flanges are generally cylindrical.

4. A housing assembly according to claim 1 wherein said sealing flanges are formed from a metal selected from the group consisting of platinum, niobium, titanium and tantalum; said ceramic contains a high percentage of alumina; and sealing flanges are brazed to said ceramic portions using platinum and gold.

5. A housing assembly comprising:
   a container subassembly and a base subassembly and each comprising:
   a ceramic portion having a periphery and inner and outer surfaces melting at said periphery and
   a continuous metal sealing flange having first and second portions, said first portion being brazed to said ceramic portion along its entire length around said periphery and said second portion being spaced from said ceramic portion;
   the ceramic portion of said container subassembly being dish-like with its inner surface defining a cavity, and having a plurality of electric leads brazed to and extending therethrough between said inner and outer surfaces;
   said second portions of said sealing flanges being positioned closely adjacent with the inner surfaces of said ceramic portions of said subassemblies facing each other and being welded together entirely around said sealing flanges; and
   said housing assembly further including electronic circuitry within said cavity and connected to said leads.

6. A housing assembly according to claim 5 wherein the first and second portions of said sealing flanges are disposed generally at a right angle to each other with each of said first portions being disposed generally in a single plane and projecting toward the center of the subassembly in which it is included, and said first and second portions of said sealing flanges are nested together with said second portions projecting along the periphery of the ceramic portion of said base subassembly.

7. A housing assembly according to claim 6 wherein said second portions of said sealing flanges are generally cylindrical.

8. A housing assembly according to claim 5 wherein said sealing flanges are formed from a metal selected from the group consisting of platinum, niobium, titanium and tantalum; said ceramic contains a high percentage of alumina; and said sealing flanges are brazed to said ceramic portions using platinum and gold.

9. A housing assembly according to claim 5 wherein said electronic circuitry includes a radio frequency pick up coil around the periphery of said cavity.

10. A method for forming a housing assembly that can be used subcutaneously, the method comprising the steps of:
    providing two ceramic portions having a periphery and inner and outer surfaces meeting at said periphery, one of the ceramic portions being dish-like with its inner surface defining a cavity, and having a plurality of through openings extending therethrough between its inner and outer surfaces;
    providing two continuous metal sealing flanges having first and second portions;
    brazing the first portion of each of the flanges along its entire length around the periphery of a different one of the ceramic portions with its second portion spaced from the ceramic portion;
    inserting wire leads through the openings in the dish-like ceramic portion;
    brazing the leads to the dish like ceramic portion where they pass through the openings;
    positioning electronic components in the cavity and connecting the electronic components to the leads;
    positioning the second portions of the sealing flanges closely adjacent with the inner surfaces of the ceramic portions of said subassemblies facing each other; and
    welding the second portions of the sealing flanges together entirely around the sealing flanges.

11. A method according to claim 10 wherein the sealing flanges are formed from a metal selected from the group consisting of platinum, niobium, titanium and tantalum; the ceramic contains a high percentage of alumina; and said brazing steps use a brazing metal consisting of platinum and gold.

* * * * *

UNITED STATES PATENT AND TRADEMARK OFFICE
CERTIFICATE OF CORRECTION

PATENT NO. : 4,785,827

DATED : November 22, 1988

INVENTOR(S) : David J. Fischer

It is certified that error appears in the above—identified patent and that said Letters Patent is hereby corrected as shown below:

Col. 3, line 24, "potion" should read --portion--.

Col. 5, line 2, "flanges" should read --flange--.

Col. 5, line 21, "melting" should read --meeting--.

Signed and Sealed this

Eighteenth Day of July, 1989

Attest:

DONALD J. QUIGG

Attesting Officer

Commissioner of Patents and Trademarks